US009938556B2

(12) United States Patent
Jeon et al.

(10) Patent No.: US 9,938,556 B2
(45) Date of Patent: *Apr. 10, 2018

(54) REAGENT COMPOSITION FOR BIOSENSOR AND BIOSENSOR HAVING THE SAME

(71) Applicant: INFOPIA CO., LTD., Anyang-si, Gyeonggi-do (KR)

(72) Inventors: Sung-Il Jeon, Yongin-si (KR); Sung-Kwon Jung, Anyang-si (KR); Seung-Min Im, Anyang-si (KR); Eun-Sang Lee, Anyang-si (KR); Se-Ho Kim, Yongin-si (KR); Hong-Seong Suk, Anyang-si (KR); Won-Dong Kim, Anyang-si (KR); Jae-Min Koh, Gunpo-si (KR)

(73) Assignee: Osang Healthcare Co., Ltd., Anyang-si (KR)

( * ) Notice: Subject to any disclaimer, the term of this patent is extended or adjusted under 35 U.S.C. 154(b) by 4 days.

This patent is subject to a terminal disclaimer.

(21) Appl. No.: 15/088,067

(22) Filed: Mar. 31, 2016

(65) Prior Publication Data

US 2016/0215320 A1 Jul. 28, 2016

Related U.S. Application Data

(63) Continuation of application No. 14/318,161, filed on Jun. 27, 2014, now Pat. No. 9,493,808.

(30) Foreign Application Priority Data

Jul. 2, 2013 (KR) .................. 10-2013-0077335

(51) Int. Cl.
*C12Q 1/00* (2006.01)
*G01N 27/327* (2006.01)
(Continued)

(52) U.S. Cl.
CPC ............ *C12Q 1/006* (2013.01); *C12Q 1/001* (2013.01); *C12Q 1/004* (2013.01); *C12Q 1/005* (2013.01);
(Continued)

(58) Field of Classification Search
CPC .................................................. G01N 27/3272
See application file for complete search history.

(56) References Cited

U.S. PATENT DOCUMENTS 5,264,348 A    11/1993  Schick et al.
7,695,608 B2    4/2010  Kim et al.
(Continued)

FOREIGN PATENT DOCUMENTS

EP    1 921 154 A1    5/2008
EP    1921154 A1      5/2008
(Continued)

OTHER PUBLICATIONS

Notice of Allowance dated May 6, 2016, issued in a parent U.S. Appl. No. 14/318,161 (10 pages).
Zhao et al., "Study on Glucose Biosensor with Naphthol Green B as a New Mediator," Journal of Southwest China Normal University (Natural Science), Oct. 2003, vol. 28, No. 5, pp. 710-714.
Extended European Search Report dated Dec. 12, 2014, issued in corresponding EP Patent Application No. 14175390.5 (9 pages).
(Continued)

*Primary Examiner* — Gurpreet Kaur
(74) *Attorney, Agent, or Firm* — Lewis Roca Rothgerber Christie LLP (57) ABSTRACT

This invention discloses a reagent composition for a biosensor having high sensitivity which is capable of improving analysis linearity of an analyte such as glucose by reacting an oxidoreductase, a metal-containing complex, and Naphthol Green B, and minimizing blood necessary for measuring blood glucose since it is possible to detect a concentration of a small amount of the analyte, and a biosensor having the same. The reagent composition for a biosensor includes at least two kinds of electron transfer mediators including Naphthol Green B, and an enzyme.

18 Claims, 4 Drawing Sheets

(51) Int. Cl.
*C12Q 1/26* (2006.01)
*C12Q 1/54* (2006.01)

(52) U.S. Cl.
CPC ............. *C12Q 1/26* (2013.01); *C12Q 1/54* (2013.01); *G01N 27/3273* (2013.01)

(56) References Cited

U.S. PATENT DOCUMENTS

| | | | |
|---|---|---|---|
| 9,493,808 B2 * | 11/2016 | Jeon | C12Q 1/004 |
| 2007/0235346 A1 | 10/2007 | Popovich et al. | |
| 2007/0295616 A1 | 12/2007 | Harding et al. | |
| 2009/0148593 A1 | 6/2009 | Jung et al. | |

FOREIGN PATENT DOCUMENTS

| | | |
|---|---|---|
| KR | 10-1239381 B1 | 3/2013 |
| TW | 200839232 A | 10/2008 |
| WO | 2013/048087 A2 | 4/2013 |
| WO | WO 2013/048087 A2 | 4/2013 |

OTHER PUBLICATIONS

C.-X. Cai et al., "Electrochemical Characterization of Electropolymerized Film of Naphthol Green B and Its Electrocatalytic Activity toward NADH Oxidation," Microchemical Journal, Feb. 1, 1998, vol. 58, No. 2, pp. 197-208, China, cited in Extended European Search Report dated Dec. 12, 2014 (12 pages).
A. Chaubey et al., "Mediated biosensors," Biosensors and Bioelectronics, Jun. 1, 2002, vol. 17, No. 6-7, pp. 441-456, cited in Extended European Search Report dated Dec. 12, 2014 (16 pages).
European Search Report, dated Nov. 7, 2017, Application No. 17185090.2-1405, 11 pages.
Zhao, et al.; Study on Glucose Biosensor with Naphthol Green B as a New Mediator; Journal of Southwest China Normal University (Natural Science); vol. 28, No. 5, Oct. 2003, pp. 710-714.
Cai, et al.; Electrochemical Characterization of Electropolymerized Film of Naphthol Green B and its Electrocatalytic Activity Toward NADH Oxidation; Microchemical Journal 58, pp. 197-208, 1998; Article No. MJ971549.
Chaubey, et al.; Mediated biosensors; Biosensors & Bioelectronics 17, 2002, pp. 441-456.

* cited by examiner

REAGENT COMPOSITION FOR BIOSENSOR AND BIOSENSOR HAVING THE SAME

CROSS-REFERENCE TO RELATED APPLICATION(S)

This application is a Continuation of U.S. application Ser. No. 14/318,161, filed Jun. 27, 2014, which claims priority to Korean Patent Application No. 10-2013-0077335, filed on Jul. 2, 2013, the disclosure of which is incorporated herein by reference in its entirety.

BACKGROUND

1. Field

The present invention relates to a reagent composition for a biosensor having high sensitivity, which is capable of improving analysis linearity of an analyte such as glucose, detecting a concentration of a small amount of analyte, and minimizing blood necessary for measuring blood glucose, and a biosensor having the same.

2. Discussion of Related Art

The present invention relates to a reagent composition for a biosensor and a biosensor having the same, and particularly, to a reagent composition for quantifying a specific ingredient of a biological sample and a biosensor having the same.

Recently, as the number of diabetic patients increases, necessity of periodically measuring an amount of blood glucose has been increased in order to diagnose and prevent diabetes. Such diabetes is known as a major health risk factor. In general, American Diabetes Association (ADA) recommends that most insulin-dependent diabetic patients check the blood glucose three or more times per day. Insulin controls use of blood sugar and prevents hyperglycemia that may cause ketosis when diabetes is not treated. However, inappropriate management of an insulin therapy may cause hypoglycemia. Since hypoglycemia may cause a coma, it may be fatal for patients.

In addition, when patients suffer from diabetes for a long time, complications such as heart disease, atherosclerosis, blindness, a stroke, hypertension, and renal failures may be caused. Since an amount of insulin injection is associated with an amount of the blood glucose, accurate detection of the blood glucose is essential to appropriately treat diabetes.

Accordingly, various blood glucose meters are produced such that the blood glucose may be easily measured using portable instruments. In general, in the blood glucose meters, each user uses a strip-type biosensor. An operating principle of such a biosensor is based on an optical method or an electrochemical method.

The biggest feature of the electrochemical method among these methods is using an electron transfer mediator. As the electron transfer mediator, ferrocene, derivatives of ferrocene; quinone, derivatives of quinone; transition metal-containing organic and inorganic materials (such as hexaamineruthenium, an osmium-containing polymer, and potassium ferricyanide); and electron transfer organic materials such as an organic conducting salt and viologen may be used.

A measurement principle of blood glucose using the electrochemical method is as follows. First, the blood glucose is oxidized to gluconate due to a catalytic action of a glucose oxidase. At this time, FAD, which is an active site of the glucose oxidase, is reduced and became $FADH_2$. Then, the reduced $FADH_2$ is oxidized to FAD through an oxidation-reduction reaction with the electron transfer mediator, and the electron transfer mediator is reduced. Electrons generated from the electron transfer mediator in a reduction state formed in this manner disperse to an electrode surface. At this time, a concentration of the blood glucose is measured by measuring a current generated by applying an oxidation potential of the electron transfer mediator in a reduction state in a working electrode surface.

Unlike a biosensor using a conventional optical method, an electrochemical biosensor using the above measurement principle may reduce an influence of oxygen, and even when sample is turbid, it is possible to use the sample without separate pretreatment.

In addition, a general electrochemical biosensor is made such that an electrode system including a plurality of electrodes is formed on an electrically insulating substrate using a method such as screen printing, and an enzyme reaction layer made of a hydrophilic polymer, an oxidoreductase, and an electron accepter is formed on the formed electrode system. When a sample solution including a substrate is dropped onto the enzyme reaction layer of the electrochemical biosensor, the enzyme reaction layer is dissolved, the substrate reacts with the enzyme, the substrate is oxidized, and therefore the electron accepter is reduced. After the enzyme reaction is completed, a concentration of the substrate in the sample solution may be obtained from an oxidation current that is obtained by electrochemically oxidizing the reduced electron accepter.

When such a biosensor is used, accurately and rapidly obtaining a measurement value using a small amount of a sample is a very important issue in terms of maximizing a user's convenience. Most products for measuring the blood glucose use a method of sampling blood and then quantifying the blood glucose in blood using a biosensor. However, since blood sampling is a considerably painful operation for the patient, it is necessary to minimize an amount of blood necessary for measurement in order to reduce the patient's pain. In particular, when 1 µl or less of a small amount of a sample is used, preferably 0.5 µl or less of a sample, and more preferably, 0.3 µl or less of a sample is used, since it is possible to sample and measure blood from an alternative site such as a forearm, it is possible to minimize resulting pain when the patient measures the blood glucose. Therefore, the biosensor needs to minimize an amount of blood necessary for measuring the blood glucose.

In addition, another issue of the biosensor is reduced measurement sensitivity according to miniaturization. An amount of a reaction-related material fixed to the electrode surface is one of major factors influencing sensitivity of the biosensor. However, recently, as the biosensors are gradually miniaturized, an area to which materials to react with a specific material may be fixed also decreases. Accordingly, there is a serious limitation of the development of a compact sensor having high sensitivity.

SUMMARY

In view of the above-described problems, the present invention provides a reagent composition for a biosensor having high sensitivity, which is capable of improving analysis linearity of an analyte such as glucose and minimizing blood necessary for measuring the analyte such as glucose.

The present invention also provides a biosensor, which uses the reagent composition and is capable of measuring an analyte such as glucose in an industrially and economically useful manner.

The above-described and other objects and effects of the present invention will be apparent from the following description which describes exemplary examples.

According to an aspect of the present invention, there is provided a reagent composition for a biosensor, wherein the reagent composition includes at least two kinds of electron transfer mediators including Naphthol Green B, and an enzyme. Here, the electron transfer mediator may further include a metal-containing complex.

Preferably, the metal-containing complex may be a ruthenium complex or a ferricyanide complex.

Preferably, the ruthenium complex may be at least one selected from the group consisting of $Ru(NH_3)_6Cl_3$, $[Ru(2,2',2''\text{-terpyridine})(1,10\text{-phenanthroline})(OH_2)]^{2+}$, trans-$[Ru(2,2'\text{-bipyridine})_2(OH_2)(OH)]^{2+}$, $[(2,2'\text{-bipyridine})_2(OH)RuORu(OH)(2,2'\text{bpy})_2]^{4+}$, and $[Ru(4,4'\text{-bipyridine})(NH_3)_5]^{2+}$.

Here, the Naphthol Green B equal to or greater than 0.1 parts by weight and equal to or less than 20 parts by weight may be used with respect to a buffer solution being 100 parts by weight.

Here, the enzyme may be any of oxidoreductase, dehydrogenase, transferase, or hydrolase.

Preferably, the oxidoreductase may be at least one selected from the group consisting of flavin adenine dinucleotide-glucose dehydrogenase, nicotinamide adenine dinucleotide-glucose dehydrogenase, pyrroloquinoline quinone glucose dehydrogenase, glutamate dehydrogenase, glucose oxidase, cholesterol oxidase, cholesterol esterase, lactate oxidase, ascorbic acid oxidase, alcohol oxidase, alcohol dehydrogenase, and bilirubin oxidase.

Preferably, the reagent composition may further include at least one of a surfactant, a water-soluble polymer, a fatty acid, a quaternary ammonium salt, and an enzyme stabilizer.

More preferably, the surfactant may be at least one of a nonionic surfactant, an ampholytic surfactant, a cationic surfactant, an anionic surfactant, and a natural surfactant.

More preferably, the water-soluble polymer may be at least one of a polyvinyl pyrrolidone (PVP), a polyvinyl alcohol (PVA), perfluoro sulfonate, hydroxyethyl cellulose (HEC), hydroxypropyl cellulose (HPC), carboxy methyl cellulose (CMC), cellulose acetate, and a polyamide.

Here, the reagent composition may be a reagent composition for a glucose biosensor.

According to another aspect of the present invention, there is provided a biosensor for measuring an analyte in a sample. The biosensor includes a lower substrate including at least one electrode onto which a reagent composition to react with the analyte is applied in a surface; a spacer formed on the lower substrate including a sample injection unit in a surface facing the electrode such that the sample is sucked and introduced to a position of the electrode; and an upper substrate provided on the spacer, wherein the reagent composition includes at least two kinds of electron transfer mediators including Naphthol Green B, and an enzyme.

Preferably, the electron transfer mediator may further include a metal-containing complex.

Preferably, the enzyme may be any of oxidoreductase, dehydrogenase, transferase, or hydrolase.

Preferably, the metal-containing complex may be a ruthenium complex or a ferricyanide complex.

BRIEF DESCRIPTION OF THE DRAWINGS

The above and other objects, features, and advantages of the present invention will become more apparent to those of ordinary skill in the art by describing in detail exemplary embodiments thereof with reference to the accompanying drawings, in which.

DETAILED DESCRIPTION

Hereinafter, the present invention will be described in detail with reference to examples and drawings of the present invention. These examples are only exemplarily proposed to more specifically describe the present invention, and it will be apparent by those skilled in the art that the scope of the present invention is not limited to these examples.

A composition for a biosensor according to an aspect of the present invention includes at least two kinds of electron transfer mediators including Naphthol Green B, and an enzyme.

Naphthol Green B serving as an electron transfer mediator is a sodium salt of Naphthol Green Y, has good solubility, is industrially inexpensive, and is used as a dye in various fields.

Also, the electron transfer mediator includes a metal-containing complex.

Here, as the metal-containing complex, materials that may be oxidized or reduced by reacting with enzymes such as a ferricyanide complex, potassium ferricyanide, a ruthenium complex, hexaammineruthenium chloride, ferrocene and derivatives thereof, quinone and derivatives thereof, phenazine methosulfate and derivatives thereof, p-benzoquinone and derivatives thereof, 2,6-dichlorophenolindophenol, methylene blue, nitrotetrazolium blue, and an osmium complex, may be used. Among them, as the metal-containing complex, the ruthenium complex or the ferricyanide complex is preferably used, more preferably, hexaammineruthenium chloride and potassium ferricyanide may be used, and most preferably, hexaammineruthenium chloride may be used.

The ruthenium complex in the present invention may be one selected from the group consisting of $Ru(NH_3)_6Cl_3$, $[Ru(2,2',2''\text{-terpyridine})(1,10\text{-phenanthroline})(OH_2)]^{2+}$, trans-$[Ru(2,2'\text{-bipyridine})_2(OH_2)(OH)]^{2+}$, $[(2,2'\text{-bipyridine})_2(OH)RuORu(OH)(2,2'\text{bpy})_2]^{4+}$, and $[Ru(4,4'\text{-bipyridine})(NH_3)_5]^{2+}$. The most preferable ruthenium complex is hexaammineruthenium chloride having a property in that an oxidation-reduction state is stable and reversible in an aqueous solution, a reduced electron transfer mediator does not react with oxygen, oxidation of the reduced electron transfer mediator is insensitive to pH, and it has little reaction with an electrochemical interfering material such as acetaminophene, ascorbic acid, bilirubin, dopamine, uric acid, and gentisic acid.

In addition, as the enzyme, an oxidoreductase and several kinds of hydrolases and transferases such as glucose dehydrogenase, glutamate oxaloacetate transaminase (GOT), and glutamate pyruvate transaminase (GPT) may be used.

The oxidoreductase is any of selected from the group consisting of flavin adenine dinucleotide-glucose dehydro- genase, nicotinamide adenine dinucleotide-glucose dehydrogenase, pyrroloquinoline quinone glucose dehydrogenase, glutamate dehydrogenase, glucose oxidase, cholesterol oxidase, cholesterol esterase, lactate oxidase, ascorbic acid oxidase, alcohol oxidase, alcohol dehydrogenase, and bilirubin oxidase. Therefore, when one is selected from among oxidoreductases, a sample analyte reacting therewith is selected and a reagent composition is prepared, it is possible to provide a biosensor for detecting any of glucose, cholesterol, lactate, glutamate, and alcohol.

As will be described below, it can be seen that, in the example of the present invention using hexaammineruthenium chloride and Naphthol Green B together, glucose detection performance significantly increases.

The electron transfer mediator may be appropriately determined by samples or an oxidoreductase to be used. Also, two kinds or more of electron transfer mediators including Naphthol Green B may be combined and used.

A content of the electron transfer mediator is not specifically limited but may be appropriately regulated by an addition amount of the sample and the like. The electron transfer mediator is preferably prepared as a buffer solution such as glycine.

Meanwhile, the following Reaction Formula represents a measurement principle of an electrochemical sensor using an oxidoreductase and an electron transfer mediator.

[Reaction Formula]

In the Reaction Formula, the electron transfer mediating material in a reduction state generated by reacting with an analyte in a sample is proportional to a concentration of the analyte in the sample. Using this proportion, based on a reference electrode or an auxiliary electrode, a constant voltage is applied to a working electrode to oxidize the electron transfer mediating material in a reduction state. A level of an oxidation current generated at this time is measured to quantify of the analyte in the sample.

As described above, the enzyme reacts with various metabolites to be measured and is reduced. Then, the reduced enzyme reacts with the electron transfer mediator and the metabolite is quantified.

In addition, the reagent composition for a biosensor according to the aspect of the present invention may further include at least one of a surfactant, a water-soluble polymer, a fatty acid, a quaternary ammonium salt, and an enzyme stabilizer.

By containing the surfactant, fixing of an oxidoreductase to the electrode is significantly inhibited and prevented. As a result, it is possible to improve conversion efficiency from an oxidized form electron carrier to a reduced form electron carrier due to an oxidoreductase in the vicinity of the electrode. In other words, it is possible to further increase a correlation with a substrate concentration in the sample solution. An amount and a form of the surfactant may be selectively regulated in order to avoid a degeneration effect in the enzyme.

The surfactant is not particularly limited, as long as an enzyme activity of the present invention is not decreased. For example, at least one of a nonionic surfactant, an ampholytic surfactant, a cationic surfactant, an anionic surfactant, and a natural surfactant may be appropriately selected and used. These may be used alone or in mixtures thereof. A preferable surfactant is polyoxyethylene ether.

More preferably, t-octylphenoxypolyethoxyethanol may be purchased (a trademark: Triton X-100) and used. A concentration of Triton X-100 in a reagent mixture is preferably 0.01 to 2 parts by weight with respect to 100 parts by weight of a buffer solution.

In addition, the water-soluble polymer among the additives is a polymer scaffold of the reagent composition that stabilizes and disperses the enzyme. As the water-soluble polymer, at least one of a polyvinyl pyrrolidone (PVP), a polyvinyl alcohol (PVA), perfluoro sulfonate, hydroxyethyl cellulose (HEC), hydroxypropyl cellulose (HPC), carboxy methyl cellulose (CMC), cellulose acetate, and a polyamide may be used.

While the present specification describes the biosensor for measuring blood glucose as an example for convenience of description, it is also possible to quantify concentrations of various metabolites, for example, biological samples such as cholesterol, lactate, creatinine, protein, hydrogen peroxide, alcohol, amino acid, and enzymes such as glutamate pyruvate transaminase (GPT) and glutamate oxaloacetate transaminase (GOT), and various organic materials or inorganic materials in an environmental sample, an agricultural and industrial sample, or a food sample, using the same method, by introducing an electron transfer mediator that is appropriate to a specific enzyme similar to application of a blood glucose test.

Therefore, it should be understood that the present invention may be used to quantify various metabolites by changing kinds of enzymes included in the reagent composition described in the present specification. For example, blood glucose oxidase, lactate oxidase, cholesterol oxidase, glutamate oxidase, horseradish peroxidase, alcohol oxidase, and the like may be used to quantify cholesterol, lactate, glutamate, hydrogen peroxide, and alcohol. An oxidase selected from the group consisting of glucose oxidase (GOx), glucose dehydrogenase (GDH), cholesterol oxidase, a cholesterol esterase, lactate oxidase, ascorbic acid oxidase, alcohol oxidase, alcohol dehydrogenase, bilirubin oxidase, and glucose dehydrogenase is preferably used.

Figure 1:
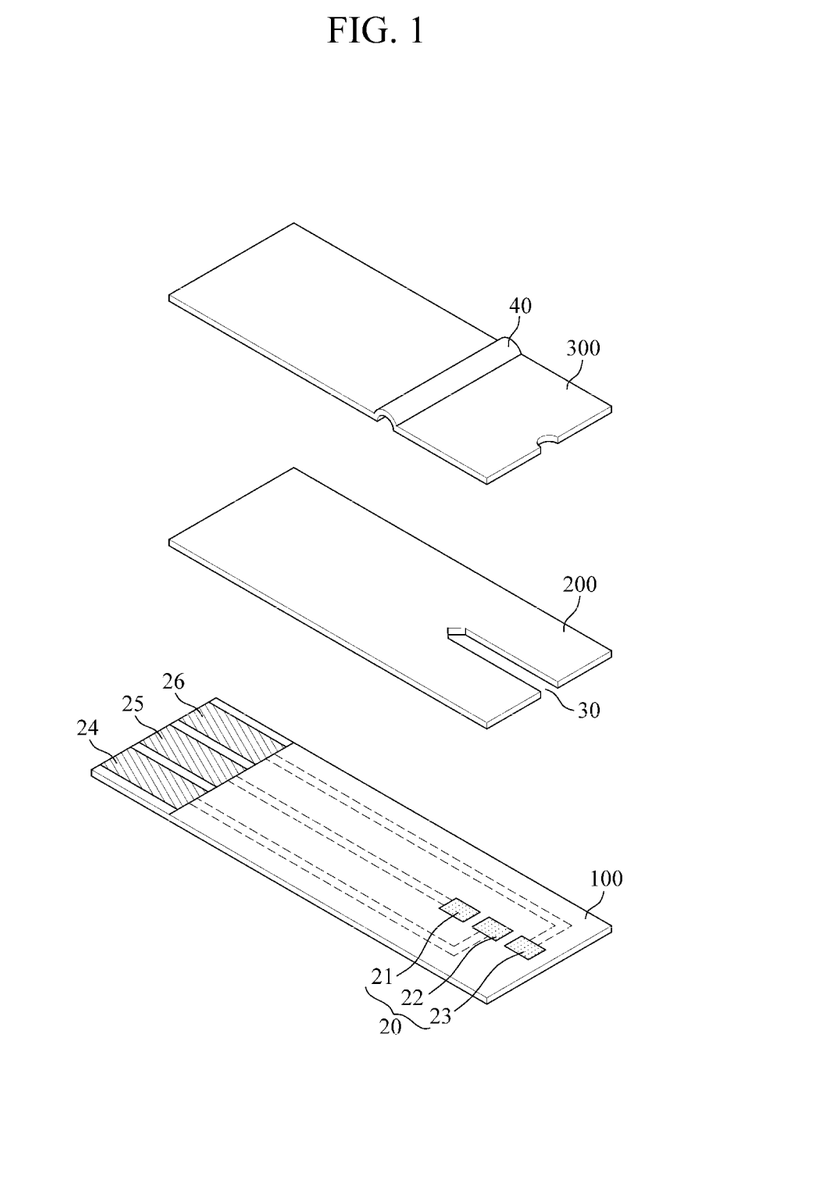
FIG. 1 is an exploded perspective view of a biosensor according to an embodiment of the present invention.

Next, an embodiment of a biosensor will be described in detail with reference to FIG. 1, an exploded perspective view of the biosensor according to another aspect of the present invention.

The biosensor according to another aspect of the present invention may be applied to conventional known sensors such as a triglyceride sensor and a cholesterol sensor. The biosensor having a reagent composition according to the present invention is mainly constituted by a lower substrate 100, a spacer 200, and an upper substrate 300.

The lower substrate 100 is an insulating substrate in which at least one of electrodes 21 to 23 are provided on a surface and the above-described reagent composition that reacts with the analyte in the sample is applied onto the electrode.

The spacer 200 is formed on the lower substrate 100 and may be bound between the lower substrate 100 and the upper substrate 300. A sample injection unit 30 may be further provided at a side surface facing the electrode such that an analyte sample is sucked and induced to the electrodes 21 to 23 of the lower substrate 100.

The upper substrate 300 is an insulating substrate that faces the lower substrate 100, is provided on the spacer 200, and further includes an air discharge unit 40 configured to discharge air that is sucked together with the analyte sample through the sample injection unit 30.

In this case, in order to increase a suction rate of the sample, the air discharge unit 40 may be formed in a tunnel shape in a layer separate from the sample injection unit 30.

In particular, the air discharge unit 40 may preferably have a semi-cylindrical shape that is formed in a direction perpendicular to a suction direction of the sample.

More specifically, the lower substrate 100 may use a thin plate made of an insulating material such as polyethylene terephthalate (PET), polystyrene, polypropylene, polyimide, an acrylic resin, polyester, PVC, or polycarbonate. The lower substrate 100 may use an insulating material having a thickness of 50 to 400 μm, more preferably, an insulating material having a thickness of 100 to 300 μm.

Lead wires 24 to 26 in contact with a measurement device (not illustrated) and an electrode system 20 in which the electrodes 21 to 23 connected to the lead wires and configured to detect an electrical signal flowing in the sucked sample are printed are formed on the top of the lower substrate 100. Here, the electrodes may include a working electrode 23, a reference electrode 22, and a check electrode 21. The lead wires 24 to 26 may be formed by a method such as general screen printing. In addition, the electrodes 21 to 23 may be formed by a screen printing method using conductive carbon ink (carbon paste).

Meanwhile, in order to mutually insulate the electrodes 21 to 23, a part other than some upper surfaces of the electrodes 21 to 23 may be partially coated with an insulator (insulating paste) to form an insulating layer. Non-conductive screen printing ink or insulating ink may be used as such an insulator.

As described above, among a part other than the part in which the insulator is partially printed, exposed upper surfaces of the electrodes 21 to 23 are coated with the reagent composition. The reagent composition includes the enzyme to react with the injected sample and the electron transfer mediator (electron accepter) as described above. The reagent composition is applied onto the electrode and fixed thereto so as to sufficiently cover the electrodes 21 to 23. In addition, the reagent composition may be applied onto all of, at least one of the electrodes 21 to 23, or only the working electrode 23 and used.

When the sample including the analyte is injected into the reagent composition through the sample injection unit 30, the analyte included in the sample reacts with the enzyme, the analyte is oxidized, and accordingly the electron accepter is reduced. After an enzyme reaction is completed, an oxidation current obtained by electrochemically oxidizing the reduced electron accepter is measured by a measurement device (not illustrated) in contact with the lead wires 24 to 26 connected to the electrodes 21 to 23. Therefore, it is possible to measure a concentration of the analyte included in the sample.

The spacer 200 forms a capillary through the sample injection unit 30 that is formed by bonding the upper substrate 300 and the lower substrate 100. This allows the analyte sample to be quickly absorbed.

The spacer 200 may be made of a double-sided tape. The sample to be measured is automatically injected through the sample injection unit 30 due to a capillary phenomenon. Air in the sample injection unit 30 is discharged externally through the air discharge unit 40 formed in the upper substrate 300 due to introduction of the sample.

Meanwhile, the electrodes 21 to 23 according to the present invention are manufactured by using a conductive polymer, carbon, ITO particles, metal particles, graphite, and platinum-treated carbon, silver, gold, palladium, or a platinum component. For example, ink made of carbon or platinum-treated carbon, or palladium-containing ink is used to print the electrodes 21 to 23 on the lower substrate 100.

In addition, the electrodes 21 to 23 may be formed on the lower substrate 100 by vacuum deposition using gold.

Hereinafter, configurations of the present invention and resulting effects will be described in detail with reference to Examples and Comparative Examples. However, the present examples are provided to describe the present invention more specifically, and the scope of the present invention is not limited to these Examples.

Example 1

Reagent Composition Preparation pH 6.5 and 50 mM of an ACES buffer solution (ACES: N-(2-acetamido)-2-aminoethanesulfonic acid) was prepared. A polyethylene glycol being 0.6 parts by weight was put into the prepared buffer solution being 100 parts by weight and dissolved. Then, a surfactant t-octylphenoxypolyethoxyethanol being 0.1 parts by weight (TritonX-100) and an enzyme stabilizer (D-(+)-Trehalose dihydrate) being 1.4 parts by weight were sequentially added and dissolved.

Hexaammineruthenium chloride $(Ru(NH_3)_6Cl_3)$ being 2.3 parts by weight, Naphthol Green B being 0.9 parts by weight, and flavin adenine dinucleotide-glucose dehydrogenase (FAD-GDH) being 0.15 parts by weight were sequentially added and dissolved in the solution, and thus the reagent composition was prepared.

Biosensor Preparation

A working electrode, a reference electrode, and a check electrode were formed on a polyester lower substrate by a screen printing method using a conducting carbon paste. The electrodes were dried for 20 minutes at 120° C. using a dry oven, and then an insulating paste was applied using the screen printing method.

The working electrode was coated with 1 mg of the reagent composition and was dried for 20 minutes at 40° C. in the dry oven. A spacer was attached to the dried lower substrate. Then, an upper substrate was covered and pressed.

Example 2

A reagent composition was prepared as in Example 1. Concentrations of compositions other than Naphthol Green B being 1.8 parts by weight were the same.

A biosensor was prepared the same as in Example 1.

Example 3

A reagent composition was prepared as in Example 1. Concentrations of compositions other than Naphthol Green B being 3.5 parts by weight were the same.

A biosensor was prepared the same as in Example 1.

Example 4

A reagent composition was prepared as in Example 1. Concentrations of compositions other than Naphthol Green B being 6.6 parts by weight were the same.

A biosensor was prepared the same as in Example 1.

Comparative Example 1

A reagent composition was prepared as in Example 1. However, the reagent composition was prepared to have a concentration of hexaammineruthenium chloride being 1.5 parts by weight, FAD-GDH being 0.15 parts by weight, and having no Naphthol Green B.

A biosensor was prepared the same as in Example 1.

Comparative Example 2

A reagent composition was prepared as in Example 1. However, the reagent composition was prepared to have a concentration of hexaammineruthenium chloride being 3.1 parts by weight, FAD-GDH being 0.15 parts by weight, and having no Naphthol Green B.

A biosensor was prepared the same as in Example 1.

Comparative Example 3

A reagent composition was prepared as in Example 1. However, the reagent composition was prepared to have a concentration of hexaammineruthenium chloride being 4.6 parts by weight, FAD-GDH being 0.15 parts by weight, and having no Naphthol Green B.

A biosensor was prepared the same as in Example 1.

Comparative Example 4

A reagent composition was prepared as in Example 1. However, the reagent composition was prepared to have a concentration of Naphthol Green B being 4.4 parts by weight, FAD-GDH being 0.15 parts by weight, and having no hexaammineruthenium chloride.

A biosensor was prepared the same as in Example 1.

Comparative Example 5

A reagent composition was prepared as in Example 1. However, the reagent composition was prepared to have a concentration of Naphthol Green B being 8.8 parts by weight, FAD-GDH being 0.15 parts by weight, and having no hexaammineruthenium chloride.

A biosensor was prepared the same as in Example 1.

Comparative Example 6

A reagent composition was prepared as in Example 1. However, the reagent composition was prepared to have a concentration of Naphthol Green B being 13.2 parts by weight, FAD-GDH being 0.15 parts by weight, and having no hexaammineruthenium chloride.

A biosensor was prepared the same as in Example 1.

Experimental Example

The biosensors prepared by Examples and Comparative Examples were used to measure a current in a glucose standard solution. Here, the glucose standard solution refers to blood in which blood taken from veins has 42% of hematocrit and has several glucose concentrations using a glucose analyzer (manufacturer: YSI Inc., model name: YSI 2300 STAT Plus).

Figure 2:
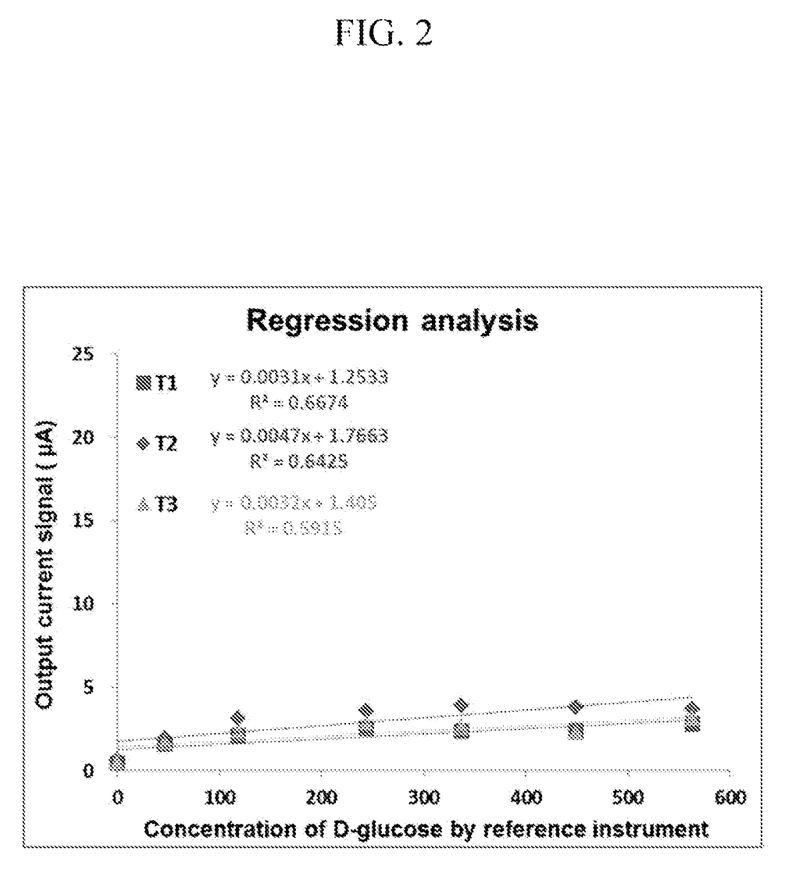
FIG. 2 is a glucose measurement current change graph according to Comparative Examples 1 to 3 of the present invention.

FIG. 2 is a glucose measurement current change graph according to Comparative Examples 1 to 3 of the present invention. In FIG. 2, T1 represents an experiment result of Comparative Example 1 including hexaammineruthenium chloride being 1.5 parts by weight and FAD-GDH being 0.15 parts by weight. T2 represents an experiment result of Comparative Example 2 including hexaammineruthenium chloride being 3.1 parts by weight and FAD-GDH being 0.15 parts by weight. T3 represents an experiment result of Comparative Example 3 including hexaammineruthenium chloride being 4.6 parts by weight and FAD-GDH being 0.15 parts by weight.

Example experiments were performed using the biosensors according to Comparative Examples 1 to 3. As a result, it was determined that the current measured by the glucose concentration did not gradually increase and linearity was not secured in the biosensor having no Naphthol Green B among the reagent compositions.

Figure 3:
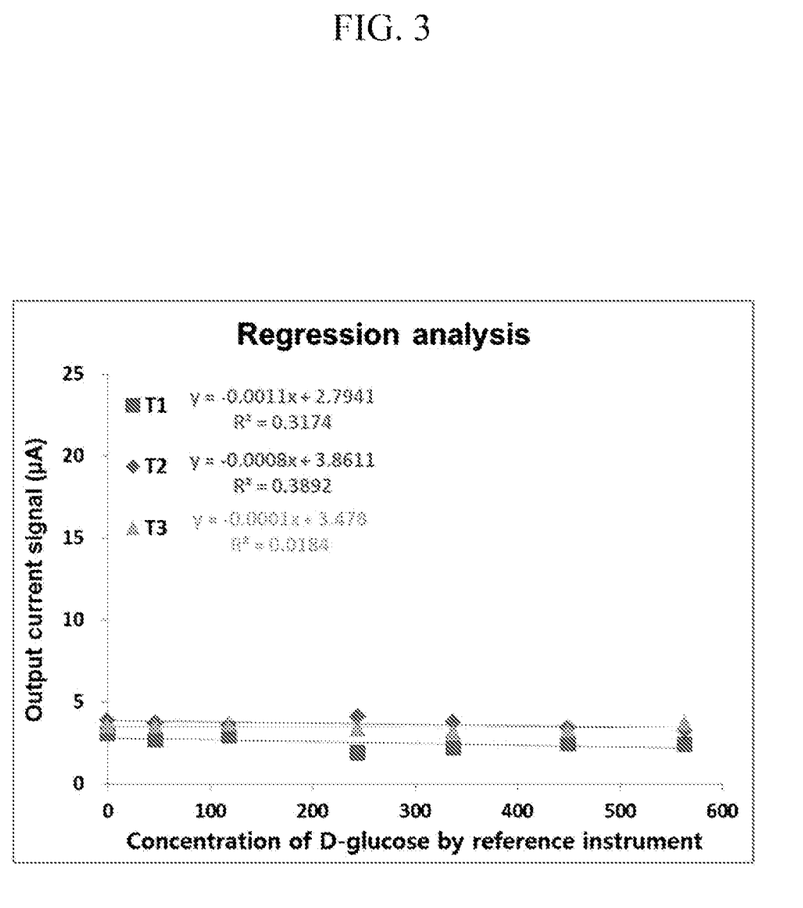
FIG. 3 is a glucose measurement current change graph according to Comparative Examples 4 to 6 of the present invention.

FIG. 3 is a glucose measurement current change graph according to Comparative Examples 4 to 6 of the present invention. In FIG. 3, T1 represents an experiment result of Comparative Example 4 including Naphthol Green B being 4.4 parts by weight and FAD-GDH being 0.15 parts by weight. T2 represents an experiment result of Comparative Example 5 including Naphthol Green B being 8.8 parts by weight and FAD-GDH being 0.15 parts by weight. T3 represents an experiment result of Comparative Example 6 including Naphthol Green B being 13.2 parts by weight and FAD-GDH being 0.15 parts by weight.

Example experiments were performed using the biosensors according to Comparative Examples 4 to 6. As a result, it was determined that the current measured by the glucose concentration did not gradually increase and linearity was not secured in the biosensor having no hexaammineruthenium chloride among the reagent compositions.

Figure 4:
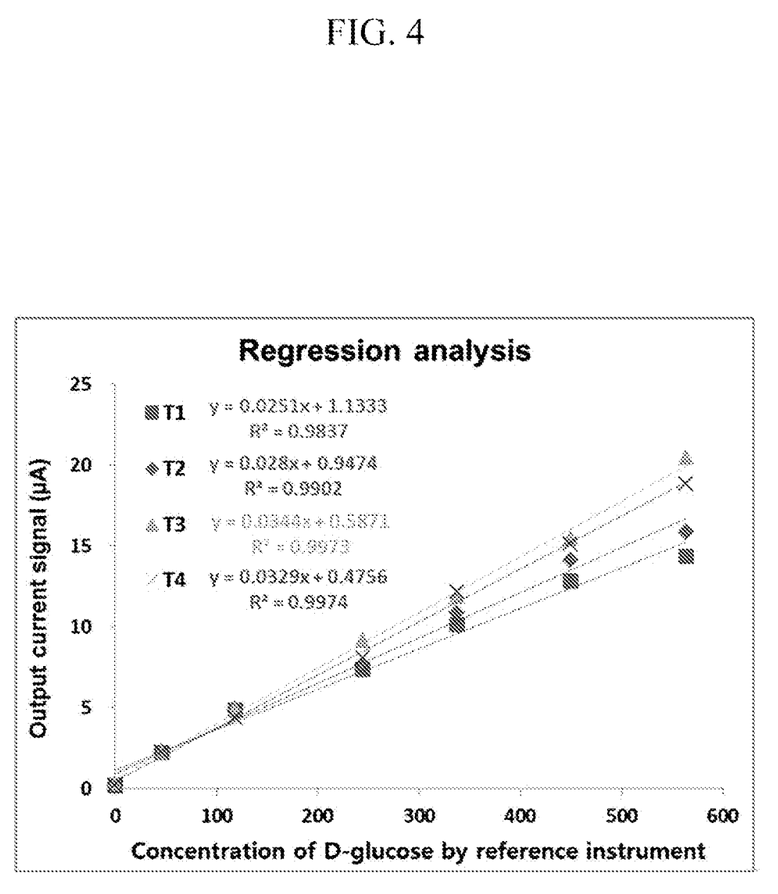
FIG. 4 is a glucose measurement current change graph according to Examples 1 to 4 of the present invention.

FIG. 4 is a glucose measurement current change graph according to Examples 1 to 4 of the present invention. In FIG. 4, T1 represents an experiment result of Example 1 including Naphthol Green B being 0.9 parts by weight, hexaammineruthenium chloride being 2.3 parts by weight, and FAD-GDH being 0.15 parts by weight. T2 represents an experiment result of Example 2 including Naphthol Green B being 1.8 parts by weight, hexaammineruthenium chloride being 2.3 parts by weight, and FAD-GDH being 0.15 parts by weight. T3 represents an experiment result of Example 3 including Naphthol Green B being 3.5 parts by weight, hexaammineruthenium chloride being 2.3 parts by weight, and FAD-GDH being 0.15 parts by weight. Finally, T4 represents an experiment result of Example 4 including Naphthol Green B being 6.6 parts by weight, hexaammineruthenium chloride being 2.3 parts by weight, and FAD-GDH being 0.15 parts by weight.

Example experiments were performed using the biosensors according to Examples 1 to 4. As a result, in general, it was determined that the current measured by the glucose concentration gradually increased as the concentration of Naphthol Green B increases. In addition, it was determined that linearity was improved as the concentration of Naphthol Green B increases. Particularly, it was determined that the best linearity was shown when the concentration of Naphthol Green B was 3.5 parts by weight.

In order to induce an appropriate reaction, the reagent composition according to another aspect of the present invention may preferably use Naphthol Green B having a concentration equal to or greater than 0.1 parts by weight and equal to or less than 20 parts by weight, and more preferably use Naphthol Green B having a concentration equal to or greater than 1 part by weight and equal to or less than 5 parts by weight, with respect to 100 parts by weight of a buffer solution. This is because Naphthol Green B having a concentration less than 5 parts by weight may cause an output signal from the reaction to be low, thus disadvantageously making it impossible to secure linearity, and, on the other hand, Naphthol Green B having a concentration greater than 20 parts by weight may lead to a deterioration of solubility of the reagent composition, which can cause failure in securing linearity and reproducibility. Most preferably, the reagent composition may use Naphthol Green B having a concentration equal to 3.5 parts by weight with respect to 100 parts by weight of a buffer solution.

Meanwhile, in the electrochemical biosensor according to the example of the present invention, the working electrode, the reference electrode, and the check electrode may be provided on a plane surface of the lower substrate. However, the working electrode, the reference electrode, and the check electrode may also be provided on different surfaces (for example, an upper substrate) so as to face each other.

According to the present invention, it is possible to improve analysis linearity of an analyte and minimize blood necessary for measuring the blood glucose since a concentration of a small amount of analyte may be detected.

Since Naphthol Green B of the reagent composition of the biosensor according to the present invention has good solubility, it is easy to be industrially used, and is also cheap. Accordingly, it is possible to provide a cheap biosensor, which is very useful for people who need to measure the blood glucose several times for a day.

However, the effects of the present invention are not limited to the above-mentioned effects. Other unmentioned effects may be clearly understood by those skilled in the art from the following description.

While detailed examples of the present invention have been specifically described above, it is apparent by those skilled in the art that various modifications and alternatives may be made within the scope of the present invention, and it may be understood that such modifications and alternatives fall within the appended claims.

What is claimed is:

1. A reagent composition for a biosensor to determine presence or concentration of a predetermined analyte in a test sample, the reagent composition comprising:
    a first electron transfer mediator of Naphthol Green B;
    a second electron transfer mediator; and
    an enzyme,
    wherein the Naphthol Green B equal to or greater than 1 parts by weight and equal to or less than 5 parts by weight is used with respect to a buffer solution being 100 parts by weight.

2. The reagent composition according to claim 1, wherein the second electron transfer mediator includes a metal-containing complex.

3. The reagent composition according to claim 2, wherein the metal-containing complex is a ruthenium complex or a ferricyanide complex.

4. The reagent composition according to claim 3, wherein the ruthenium complex is at least one selected from the group consisting of $Ru(NH_3)_6Cl_3$, $[Ru(2,2',2''\text{-terpyridine})(1,10\text{-phenanthroline})(OH_2)]^{2+}$, trans-$[Ru(2,2'\text{-bipyridine})_2(OH_2)(OH)]^{2+}$, $[(2,2'\text{-bipyridine})_2(OH)RuORu(OH)(2,2'bpy)_2]^{4+}$, and $[Ru(4,4'\text{-bipyridine})(NH_3)_5]^{2+}$.

5. The reagent composition according to claim 1, wherein the enzyme is any of oxidoreductase, dehydrogenase, transferase, or hydrolase.

6. The reagent composition according to claim 5, wherein the oxidoreductase is at least one selected from the group consisting of flavin adenine dinucleotide-glucose dehydrogenase, nicotinamide adenine dinucleotide-glucose dehydrogenase, pyrroloquinoline quinone glucose dehydrogenase, glutamate dehydrogenase, glucose oxidase, cholesterol oxidase, cholesterol esterase, lactate oxidase, ascorbic acid oxidase, alcohol oxidase, alcohol dehydrogenase, and bilirubin oxidase.

7. The reagent composition according to claim 1, wherein the reagent composition further includes at least one of a surfactant, a water-soluble polymer, a fatty acid, a quaternary ammonium salt, and an enzyme stabilizer.

8. The reagent composition according to claim 7, wherein the surfactant is at least one of a nonionic surfactant, an ampholytic surfactant, a cationic surfactant, an anionic surfactant, and a natural surfactant.

9. The reagent composition according to claim 7, wherein the water-soluble polymer is at least one of a polyvinyl pyrrolidone (PVP), a polyvinyl alcohol (PVA), perfluoro sulfonate, hydroxyethyl cellulose (HEC), hydroxypropyl cellulose (HPC), carboxy methyl cellulose (CMC), cellulose acetate, and a polyamide.

10. The reagent composition according to any one of claims 1 to 9,
    wherein the reagent composition is a reagent composition for a glucose biosensor.

11. A biosensor for measuring an analyte in a sample, the biosensor comprising:
    at least one electrode containing a reagent composition to react with an applied analyte;
    a lower substrate including the at least one electrode; and
    an upper substrate,
    wherein the lower substrate and the upper substrate are arranged in a vertical stack,
    wherein the reagent composition includes at least two kinds of electron transfer mediators including Naphthol Green B, and an enzyme, and
    wherein the Naphthol Green B equal to or greater than 1 parts by weight and equal to or less than 5 parts by weight is used with respect to a buffer solution being 100 parts by weight.

12. The biosensor according to claim 11,
    wherein the electron transfer mediator further includes a metal-containing complex.

13. The biosensor according to claim 12,
    wherein the metal-containing complex is a ruthenium complex or a ferricyanide complex.

14. The biosensor according to claim 11,
    wherein the upper substrate further includes an air discharge unit configured to discharge air in the sample.

15. The biosensor according to claim 14,
    wherein the air discharge unit has a semi-cylindrical shape that is formed in a direction perpendicular to a suction direction of the sample.

16. The biosensor according to claim 11,
    wherein the enzyme is any of oxidoreductase, dehydrogenase, transferase, or hydrolase.

17. The biosensor according to claim 11, further comprising a spacer positioned between the lower substrate and the upper substrate.

18. A biosensor for measuring an analyte in a sample, the biosensor comprising:
    at least one electrode containing a reagent composition to react with an applied analyte;
    a lower substrate including the at least one electrode; and
    an upper substrate,
    wherein the lower substrate and the upper substrate are arranged in a vertical stack, wherein the reagent composition includes at least two kinds of electron transfer mediators including Naphthol Green B, and an enzyme, and wherein the Naphthol Green B equal to or greater than 1 parts by weight and equal to or less than 20 parts by weight is used with respect to a buffer solution being 100 parts by weight.

* * * * *